United States Patent
Anumula et al.

(10) Patent No.: US 7,919,633 B2
(45) Date of Patent: Apr. 5, 2011

(54) PROCESS FOR PREPARATION OF CELECOXIB

(75) Inventors: Raghupathi Reddy Anumula, Hyderabad (IN); Goverdhan Gilla, Hyderabad (IN); Sampath Alla, Karim Nagar (IN); Thirupathi Reddy Akki, Karim Nagar (IN); Yakambram Bojja, Warangal (IN)

(73) Assignees: Dr. Reddy's Laboratories Limited, Hyderabad (IN); Dr. Reddy's Laboratories, Inc., Bridgewater, NJ (US)

( * ) Notice: Subject to any disclaimer, the term of this patent is extended or adjusted under 35 U.S.C. 154(b) by 370 days.

(21) Appl. No.: 12/051,059

(22) Filed: Mar. 19, 2008

(65) Prior Publication Data
US 2008/0234491 A1    Sep. 25, 2008

Related U.S. Application Data

(60) Provisional application No. 60/973,483, filed on Sep. 19, 2007.

(30) Foreign Application Priority Data

Mar. 19, 2007 (IN) ............................ 558 CHE/2007

(51) Int. Cl.
C07D 231/12 (2006.01)
(52) U.S. Cl. .................................. 548/377.1; 548/373.1
(58) Field of Classification Search ............... 548/373.1, 548/377.1
See application file for complete search history.

(56) References Cited

U.S. PATENT DOCUMENTS

| | | | |
|---|---|---|---|
| 5,466,823 A | 11/1995 | Talley et al. | |
| 5,563,165 A | 10/1996 | Talley et al. | |
| 7,141,678 B2 * | 11/2006 | Letendre et al. | 548/377.1 |
| 7,759,497 B2 * | 7/2010 | Letendre et al. | 548/377.1 |

OTHER PUBLICATIONS

Letendre et al (2003): STN International HCAPLUS database, (Columbus, Ohio), Accession No. 2003:951004.*

* cited by examiner

*Primary Examiner* — Golam M Shameem
(74) *Attorney, Agent, or Firm* — Thomas C. McKenzie; Robert A. Franks; Balaram Gupta

(57) ABSTRACT

There is provided a process for preparation of celecoxib by reacting 4,4,4-trifluoro-1-[4-(methyl)phenyl]butane-1,3-dione with 4-sulphonamidophenylhydrazine or its salt in a solvent medium that contains an alkyl ester. There is also provided a process for the purification of celecoxib using aromatic hydrocarbon solvents.

7 Claims, 1 Drawing Sheet

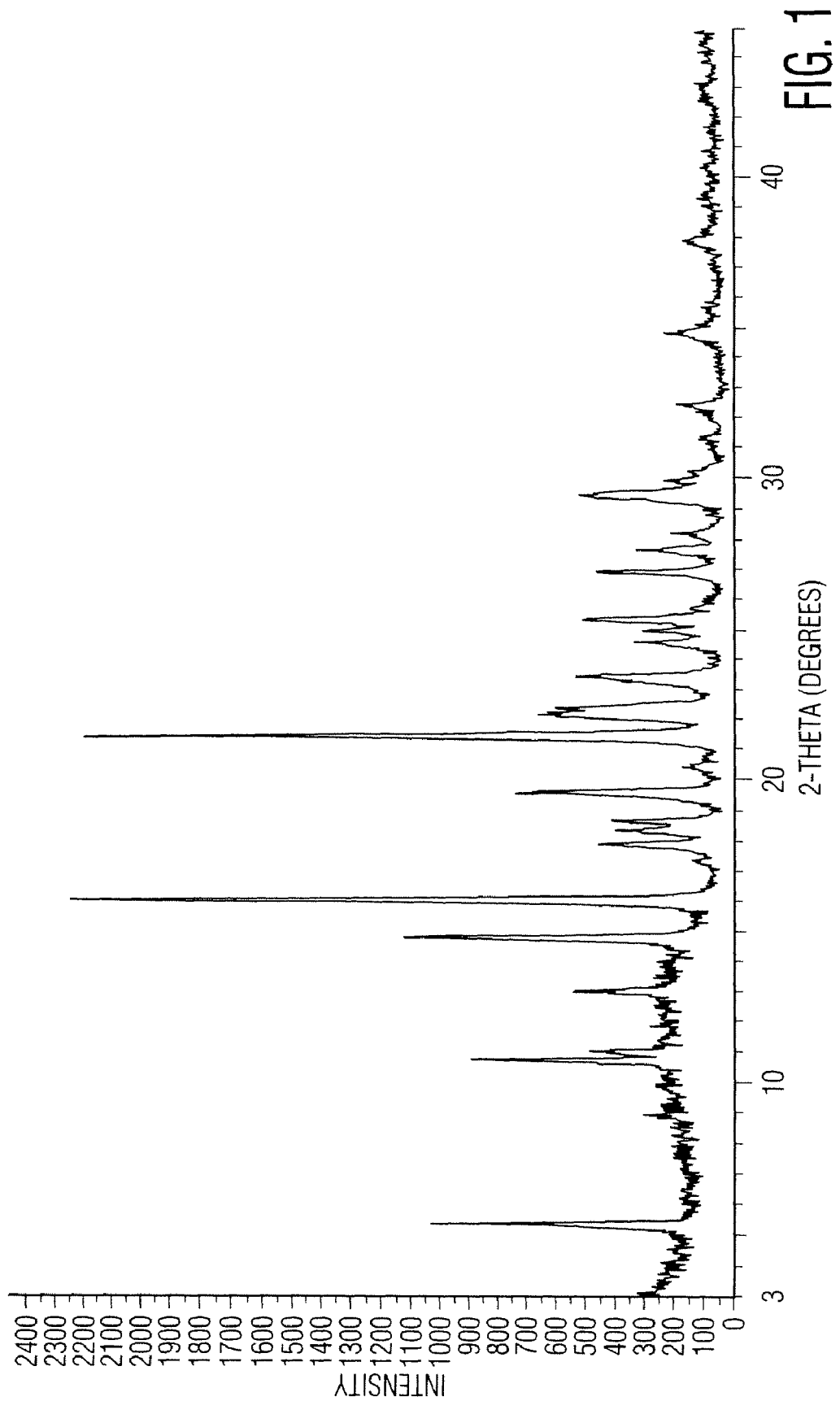

PROCESS FOR PREPARATION OF CELECOXIB

TECHNICAL FIELD

The present application relates to a process for the preparation of celecoxib.

INTRODUCTION

Celecoxib is chemically known as 4-[5-(4-methylphenyl)-3-(trifluoromethyl)-1H-pyrazol-1-yl]benzenesulfonamide and is represented by the Formula I.

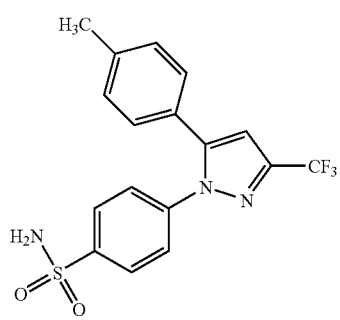

Formula I

Celecoxib is a potent and specific inhibitor of cyclooxygenase-2 and is useful in the treatment of rheumatoid arthritis, osteoarthritis, primary dysmenorrhea and acute pain. The drug is currently marketed as Celebrex in the United States of America.

U.S. Pat. No. 5,466,823 discloses celecoxib and its pharmaceutically acceptable salts, a pharmaceutical composition, and methods of treatment.

U.S. Pat. No. 5,563,165 describes the preparation of celecoxib and its pharmaceutically acceptable salts.

SUMMARY

In one aspect there is provided a process for preparation of celecoxib of the formula:

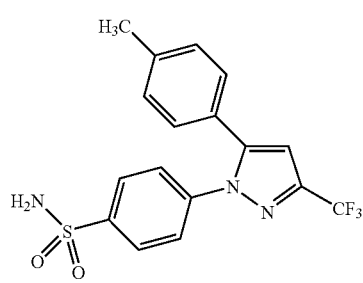

the process including reacting a compound of the formula:

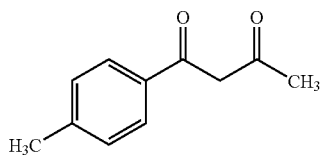

with a compound of the formula:

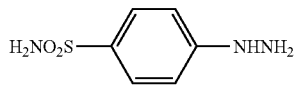

or its acid addition salt, in a solvent medium that includes an alkyl ester, water or mixtures thereof. Various embodiments and variants are provided.

In another aspect, there is provided a process for purification of celecoxib, which process includes:
(i) providing a solution of celecoxib in an aromatic hydrocarbon solvent;
(ii) causing crystallization in said solution to obtain a solid precipitate; and
(iii) isolating the solid precipitate, which is the purified celecoxib.

Various embodiments and variants are provided.

In another aspect, there is provided a purified solid celecoxib produced by the process described herein. Various embodiments and variants are provided.

In other aspects, there are provided compounds found as impurities in the processes described herein and suitable for use as standards and purified celecoxib substantially free of these impurities. Various embodiments and variants are provided.

BRIEF DESCRIPTION OF THE DRAWING

FIG. 1 is an illustrative example of X-ray powder diffraction pattern of a crystalline form of celecoxib of Formula I, prepared in accordance with illustrative example 6.

DETAILED DESCRIPTION

As used herein, the term "substantially free" with respect to presence of a component or an impurity means less than about 0.05% of the impurity is present. This definition applies only to the present patent application.

The present application provides an improved process for the preparation of celecoxib of Formula I via a reaction of 4,4,4-trifluoro-1-[4-(methyl)phenyl]-butane-1,3-dione of Formula IV with 4-sulphonamido phenylhydrazine of Formula II or its acid addition salt in a solvent medium that includes an alkyl ester, water or mixtures thereof.

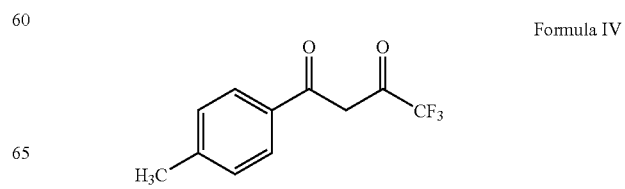

Formula IV

-continued

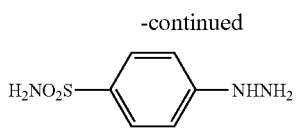

Formula II

Suitable alkyl ester solvents include, but are not limited to, ethyl acetate, n-propyl acetate, isopropyl acetate, tertiary-butyl acetate, and amyl acetate. Ethyl acetate is preferred. Preferably, the reaction is carried out in a mixture of ethyl acetate and water.

The ratio of organic solvent to water may range from about 90:10 to about 10:90 (v/v); preferably 50:50 (v/v).

The reaction may be performed at a temperature ranging from about 25° C. to about reflux temperature of the solvent or mixture of solvents used for the reaction.

The precipitation of compound from the reaction mixture may be performed by cooling the reaction mixture to a temperature from about ambient temperature to 0° C. or removal of the solvent followed by cooling the reaction mixture.

Removal of the solvent may be carried out by using evaporation, atmospheric distillation, or distillation under vacuum. The preferred method for the removal of solvent may be distillation under vacuum. The techniques that may be used for the distillation include distillation using a rotational evaporator such as a Buchi Rotavapor.

The compounds of Formula II and Formula IV may prepared by any method, including those that may be known in the art. For example, 4,4,4-Trifluoro-1-[4-(methyl)phenyl]-butane-1,3-dione compound of Formula IV may be prepared by the reaction of 4-methylacetophenone of Formula VI with an alkyl ester of trifluoro acetic acid of Formula V in the presence of a base and an organic solvent.

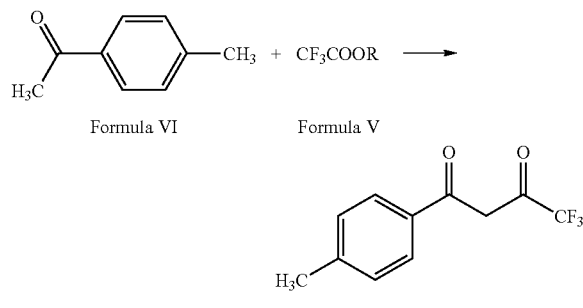

wherein R = $C_1$-$C_4$ alkyl

Suitable bases include, but are not limited to, organic bases, such as triethylamine, di-isopropylamine, N,N-di-isopropyl-ethylamine, butylamine, sodium methoxide, potassium methoxide, and potassium tertiary butoxide; inorganic bases, such as sodium hydroxide, potassium hydroxide, sodium carbonate, sodium bicarbonate, potassium carbonate, potassium bicarbonate, sodium hydride, and potassium hydride.

Examples of suitable inert solvents for the preparation of compound of Formula IV include but are not limited to, ketone solvents, such as acetone, methyl ethyl ketone, methyl isobutyl ketone, n-butanone, and tertiary-butyl ketone; nitrile solvents, such as acetonitrile, and propionitrile; halogenated solvents, such as dichloromethane, ethylene dichloride, and chloroform; esters, such as ethyl acetate, n-propylacetate, isopropyl acetate, and tertiary-butyl acetate; aprotic polar solvents, such as N,N-dimethylformamide, dimethylsulfoxide, and N,N-dimethylacetamide; ethers, such as diisopropyl ether, tetrahydrofuran and 1,4-dioxane; hydrocarbon solvents, such as cyclohexane, toluene and xylene; and mixtures thereof.

The reaction may be carried out at temperature ranging from about 25° C. to about reflux temperature of the solvent or mixture of solvents used for the reaction.

The resultant compound of Formula IV may be isolated from the reaction mixture and used in the next step. Alternatively, the reaction mixture containing the compound of the Formula IV may be used directly without isolation.

4-sulphonamido phenylhydrazine of Formula II may be prepared by the reaction of sulphanilamide of Formula III with sodium nitrite in the presence of an acid, such as hydrochloric acid, hydrobromic acid, sulfuric acid, and nitric acid; followed by reducing the resultant diazonium salt to afford the hydrazine derivate, which may be isolated in the form of an acid addition salt by reaction with an acid.

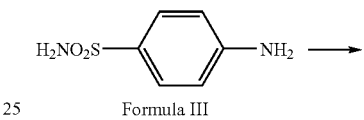

Formula III

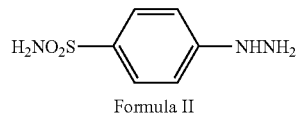

Formula II

The intermediate diazonium compound may be reduced using appropriate reagents. Examples of reducing agents include but are not limited to; tin chloride, sodium sulphite, sodium metabisulphite and the like.

The acid addition salts of compound of the formula II includes, but are not limited to, hydrochloride, hydrobromide, sulfate, nitrate, oxalate, besylate, methane sulfonate, and tartrate, preferably, hydrochloride salt.

The reaction may be preferably carried out in water as suitable solvent.

Also provided is a process for purification of celecoxib, which process includes:
  (i) providing a solution of celecoxib in an aromatic hydrocarbon solvent;
  (ii) causing crystallization in the solution to obtain a solid precipitate; and
  (iii) isolating the solid precipitate, which is the purified celecoxib.

The step of providing a solution of celecoxib includes dissolving celecoxib in an aromatic hydrocarbon solvent or obtaining such solution from a previous processing step where celecoxib is formed.

The aromatic hydrocarbon solvent used for providing solution of celecoxib may be selected from, but are not limited to, benzene, toluene, xylene, ethyl benzene and the like; and mixtures thereof. The preferred hydrocarbon solvent is toluene.

The dissolution of celecoxib in a hydrocarbon solvent may be performed at an elevated temperature, if required, to achieve desired concentration. Further, an activated charcoal treatment may be performed to remove the color impurities or to reduce the content of heavy metals, if any, or to remove the extraneous matter from the solution containing celecoxib.

The crystallization from the resultant reaction mixture may be carried out in a manner known to a person skilled in the art. For example it may be accomplished by cooling the reaction mixture to a lower temperature of about 25° C. to 0° C. or removal of the solvent followed by cooling the reaction mixture. Solvent may be removed by the techniques such as evaporation using rotational evaporator such as Buchi Rotavapor under vacuum.

The product may be isolated from the reaction mixture by any conventional techniques such as filtration by gravity, by suction, and by centrifugation.

In a preferred embodiment, celecoxib may be isolated by filtration and, if desired, the compound may be further washed with a solvent to remove the occluded mother liquor.

The obtained wet cake may be further dried by any of the conventional techniques such as drying in a tray dryer, cone vacuum drier, air oven, fluidized bed drier, spin flash dryer, flash dryer and the like. The drying may be carried out at temperature of about 25° C. to about 75° C., with or without vacuum.

Also provided are compounds of the Formula VII and the Formula VIII, which may be present as impurities in a celecoxib solid. These compounds may be used, for example, as reference standards in the analysis of celecoxib.

Formula VII

Formula VIII

A compound in a relatively pure state may be used as a "reference standard." A reference standard may be used for both qualitative and quantitative analysis to check the content of impurities in an unknown mixture. The detection or quantification of the reference standard serves to establish the level of purity of the organic compound. The management of process impurities is greatly enhanced by understanding their chemical structures and synthetic pathways and by identifying the parameters that influence the amount of impurities in the final product. The compounds of Formula VII and the Formula VIII are useful, e.g., as reference standards for analysis of celecoxib-containing products and/or celecoxib powder.

The celecoxib of Formula I obtained by the process described herein is believed to be substantially free from impurities that are originated from process and/or degradation. Typically, celecoxib obtained as described herein may have purity of at least about 99.5% by weight, preferably at least about 99.9% by weight as determined by high-performance liquid chromatography (HPLC). In particular, celecoxib obtained as described herein, in the state of a powder (active pharmaceutical ingredient) and/or in the product that contains celecoxib as active ingredient, is believed to be substantially free from related compounds of Formula VII and/or Formula VIII.

Celecoxib obtained as described herein may have residual solvent content less than about 10% by weight, preferably less than about 2% by weight, more preferably less than about 1% by weight, most preferably less than about 0.1% by weight as determined by Gas Chromatography (GC).

The $D_{10}$, $D_{50}$ and $D_{90}$ values are useful ways for indicating particle size distribution. $D_{90}$ refers to at least 90 volume percent of the particles having a size smaller than the said value. Likewise $D_{10}$ refers to 10 volume percent of the particles having a size smaller than the said value. $D_{50}$ refers to 50 volume percent of the particles having a size smaller than the said value. Methods for determining $D_{10}$, $D_{50}$ and $D_{90}$ include laser diffraction, such as using equipment from Malvern Instruments Ltd. of Malvern, Worcestershire, United Kingdom.

Celecoxib obtained as described herein preferably has a particle size of $D_{90}$ less than about 200 microns. In particular, celecoxib obtained as described herein has a particle size of $D_{90}$ less than about 150 microns, $D_{50}$ less than about 50 microns and $D_{10}$ less than about 10 microns. If desired, celecoxib may be milled to reduce the size of particles as required.

The crystalline form of celecoxib obtained by the process described herein may be characterized by its X-ray powder diffraction pattern having peaks at about 5.3, 10.6, 12.9, 14.7, 16.0, 17.8, 18.6, 19.5, 21.4, 23.3, 25.2, and 29.4±0.2 degrees 2 theta. The crystalline form of celecoxib of Formula I obtained by the process exemplified in example 6 may be further characterized by its X-ray powder diffraction pattern substantially as depicted in FIG. 1.

The X-ray powder diffraction pattern for celecoxib is obtained on a Bruker AXS, DS Advance Powder X-ray powder Diffractometer with Cu K alpha-1 radiation having wavelength 1.54 Å.

Certain specific aspects and embodiments of the present invention will be explained in more detail with reference to the following examples, which are provided by way of illustration only and should not be construed as limiting the scope of the invention in any manner.

EXAMPLES

Example 1

Preparation of 4,4,4-trifluoro-1-[4-(methyl)phenyl]-butane-1,3-dione

Sodium methoxide (25.6 g) and toluene (105 ml) were taken in a flask. A solution of 4-methylacetophenone (50 g) in toluene (52 ml) was added at 20-25° C. in 30 minutes. The resultant reaction mixture was stirred further at 20-25° C. for 30 minutes. A solution of methyltrifluoroacetate (56.8 g) in toluene (52 ml) was added slowly at 20-25° C. for about 1 hour and the reaction mixture was heated to about 110° C. for 24 hours. The reaction mixture was cooled to 30° C. and poured into a flask containing aqueous hydrochloric acid (210 ml, 3N). The layers were separated and the aqueous layer was extracted with toluene (2×50 ml). The organic layers were combined and washed with water (2×50 ml). The solvent was removed completely under vacuum to afford the title compound (Yield: 79 g).

Example 2

Process for the Preparation of 4,4,4-trifluoro-1-[4-(methyl)phenyl]-butane-1,3-dione A mixture of 4-methylacetophenone (0.85 g), isopropyltrifluoroacetate (1.0 g) and toluene (2 ml) was added to a mixture of sodium methoxide (0.4 g) and toluene (2 ml) at 35-40° C. The reaction mixture was stirred at 75° C. for 4 hours. The reaction mixture was cooled to 25-30° C. Water (2 ml) and aqueous HCl (3 ml, 20%) were added and the reaction mixture was stirred at 25-30° C. for 30 minutes. The layers were separated. Aqueous layer was extracted with toluene (2×2 ml). The organic layers were combined and the solvent was removed by distillation at 55° C. under vacuum to obtain the title compound (Yield: 1.0 g).

Example 3

Preparation of 4-sulphonamidophenylhydrazine hydrochloride

A mixture of hydrochloric acid (37 ml), water (25 ml), ice (25 g) and sulphonilamide (37 g) was cooled to −10° C. Aqueous sodium nitrite (10 g in 12 ml water) was added at −10° C.

In a separate flask an aqueous solution of sodium hydroxide (14 g in 150 ml water) was prepared and sodium metabisulphite (54 g) was added at 0-5° C. The reaction mixture was slowly added to a flask containing the above reaction mixture at 0° C. The reaction mixture was heated to 80° C. and stirred for 1 hour. Hydrochloric acid (37 ml) was added to the reaction mixture at 80° C. The reaction mixture was further stirred at 90° C. for 4 hours. The reaction mixture was cooled to 30° C. and hydrochloric acid (150 ml) was added and stirred further for 30 minutes. The separated solid was filtered, washed with isopropyl alcohol (40 ml) and dried for 2 hours (Yield: 25 g).

Example 4

Process for the Preparation of 4-sulphonamidophenylhydrazine hydrochloride

A mixture of hydrochloric acid (3 ml), water (2 ml), ice (2 g) and sulphonilamide (2 g) was cooled to −10° C. Aqueous sodium nitrite (0.8 g in 1 ml water) was added at −10° C.

In another flask an aqueous sodium hydroxide solution (1.0 g in 12 ml water) was prepared and to that sodium metabisulphite (4 g) was added at 25-30° C. Ice (2 g) was added and the reaction mixture was cooled to about 0° C. The reaction mixture was slowly added to a flask containing above reaction mixture at about 0° C. The reaction mixture was heated to 80 to 90° C. and stirred for 5 hours. Hydrochloric acid (12 ml) was added at 30-35° C. and the reaction mixture was stirred for 30 minutes. The separated solid was filtered, washed with isopropyl alcohol and dried for 2 hours (Yield: 2.0 g).

Example 5

Preparation of Celecoxib

A mixture of 4-Sulphonamidophenylhydrazine hydrochloride (10.5 g), 4,4,4-trifluoro-1-[4-(methyl)phenyl]butane-1,3-dione (10.5 g), ethyl acetate (50 ml) and water (50 ml) was heated at 75-80° C. and stirred for 5 hours. The reaction mixture was cooled to 0-5° C. and stirred for 1 hour. The separated solid was filtered, washed with water (150 ml) and dried (Yield: 27 g).

Example 6

Purification of Celecoxib

Celecoxib (25 g) obtained by the process described in example 5 was taken in toluene (375 ml) and the mixture was heated to 80° C. and stirred for 15 minutes. Activated carbon (1.2 g) was added and the reaction mixture was further heated to 80° C. and stirred for 30 minutes. The reaction mixture was cooled to 10-15° C. and stirred for an hour. The separated solid was filtered, washed with toluene and then dried at 75° C. for 6 hours to yield the title compound (Yield: 22.3 g, Purity by HPLC: 99.97% by weight; Content of compound of Formula VII is less than 0.1% by weight; Content of compound of Formula VIII is less than 0.1% by weight).

Example 7

Preparation of Celecoxib

A mixture of 4-sulphonamidophenylhydrazine hydrochloride (42.2 g), 4,4,4-trifluoro-1-[4-(methyl)phenyl]butane-1,3-dione (40 g) and methanol (860 ml) was heated to 65° C. and stirred for 10 hours. The reaction mixture was cooled to 25-30° C. and the solvent was completely removed under vacuum. The residue was taken in a mixture of ethyl acetate (332 ml) and water (80 ml) and stirred for 10 minutes. The layers were separated and the aqueous layer was extracted with ethyl acetate (2×52 ml). The organic layers were combined and washed with water (2×80 ml). The combined organic layer was treated with activated carbon at 60° C. The carbon was removed by filtration and the solvent was distilled off to a volume of about 100-115 ml and n-hexane (320 ml) was added. The reaction mixture was stirred at 30° C. for 30 minutes. The separated solid was filtered and washed with n-hexane (20 ml) (Yield: 55 g, purity 94.3%).

Example 8

HPLC Method for Analysis of Celecoxib

The amounts of impurities in celecoxib are determined using HPLC. The HPLC analysis conditions are described in Table 1.

TABLE 1

| | |
|---|---|
| Column | 5 μm, 25 cm × 4.6 mm internal diameter containing octadecylsilyl silica gel |
| Flow rate | 0.8 ml/minute |
| Detector | 258 nm |
| Injection load | 10 μl |
| Sample Preparation | 5 mg sample was dissolved in diluent and diluted to 10 ml. |
| Temperature | Ambient |
| Run Time | 60 minutes |
| Diluent | Mobile phase B |
| Mobile phases | Mobile phase A: 0.01 m of Potassium dihydrogen phosphate and 0.001 m of Octane 1-sulfonic acid sodium salt and adjust its pH to 3.3<br>Mobile phase B: mixture of Acetonitrile and water in the ratio of 70:30 (v/v). Concentration: 0.5 mg/ml in mobile phase-B. |

| Gradient program | Interval (min) | Mobile phase A (percent v/v) | Mobile phase A (percent v/v) | Elution |
|---|---|---|---|---|
| | 0-8 | 0-50 | 0-50 | Isocratic |
| | 8-42 | 50-5 | 50-95 | Liner gradient |
| | 42-45 | 5-50 | 95-50 | Liner gradient |
| | 45-60 | 50 | 50 | Isocratic |

We claim:

1. A process for preparation of celecoxib of the formula:

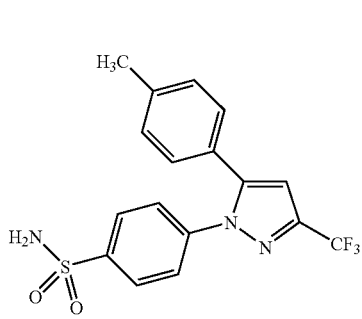

said process comprising reacting a compound of the formula:

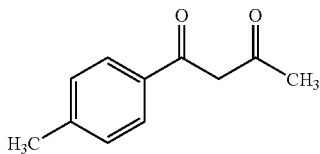

with a compound of the formula:

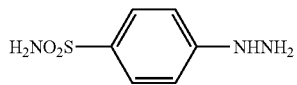

or its acid addition salt, in a solvent medium comprising an alkyl ester, water or mixtures thereof.

2. The process of claim 1, wherein said solvent medium is a mixture of an alkyl ester and water.

3. The process of claim 1, wherein the alkyl ester is selected from the group consisting of ethyl acetate, n-propyl acetate, isopropyl acetate, tertiary butyl acetate, amyl acetate and mixtures thereof.

4. The process of claim 1, wherein the alkyl ester is ethyl acetate.

5. The process of claim 2, wherein the ratio of alkyl ester to water in the solvent medium is from 10:90 to 90:10 (volume/volume).

6. The process of claim 5, wherein the ratio of alkyl ester to water is 50:50 (volume/volume).

7. The process of claim 1, wherein the reaction is carried out at a temperature above about 25° C.

* * * * *